United States Patent [19]

Haszmann et al.

[11] Patent Number: 5,354,390
[45] Date of Patent: Oct. 11, 1994

[54] PROCESS FOR OBTAINING TISSUE-PROTECTIVE IMPLANTS PREPARED FROM TITANIUM OR A TITANIUM-BASE MICROALLOY

[75] Inventors: Károly Haszmann; Lajos Kovács; Kálmán Vargha, all of Budapest; Imre Juhász, Hódmezóvás/ rhely; György Szabó, Budapest, all of Hungary

[73] Assignee: Tavkozlesi Kutato Intezet, Budapest, Hungary

[21] Appl. No.: 41,441

[22] Filed: Mar. 31, 1993

[30] Foreign Application Priority Data

Apr. 10, 1992 [HU] Hungary .............................. P92 01220

[51] Int. Cl.$^5$ .......................... C21D 11/00; C23F 13/00
[52] U.S. Cl. ................................... 148/518; 148/269; 205/318; 205/322; 623/16
[58] Field of Search .................... 427/2; 205/318, 322; 148/518, 269; 623/16

[56] References Cited

U.S. PATENT DOCUMENTS

| | | | |
|---|---|---|---|
| 4,746,532 | 5/1988 | Suzuki et al. | 427/2 |
| 4,846,837 | 7/1989 | Kurze et al. | 205/322 |
| 4,847,163 | 7/1989 | Shimamune et al. | 427/2 |
| 5,074,972 | 12/1991 | Matz | 148/269 |
| 5,160,599 | 11/1992 | Kobayashi et al. | 205/322 |
| 5,205,921 | 4/1993 | Shirkahzadeh | 427/2 |
| 5,211,663 | 5/1993 | Kovacs et al. | 427/2 |
| 5,211,832 | 5/1993 | Cooper et al. | 205/322 |

FOREIGN PATENT DOCUMENTS

| | | | |
|---|---|---|---|
| 0462894 | 3/1975 | U.S.S.R. | 205/322 |

*Primary Examiner*—Upendra Roy
*Attorney, Agent, or Firm*—Keil & Weinkauf

[57] ABSTRACT

The invention relates to a new process for obtaining tissue-protective devices of bone surgery implants prepared from a medical-purity metal, titanium and/or a titanium-base microalloy containing at least 98% by weight of titanium, by establishing a biocompatible (tissue-protective) coating on the metal surface by anodic oxidation after degreasing and chemical or electrochemical etching, which comprises carrying out the anodic oxidation of the etched implant surfaces in an aqueous solution of a phosphate concentration lower than 20% by weight with a current density of 2 to 50 mA/cm$^2$ until reaching a voltage of at least 105 V, then, after washing to ion-free, heat-treating the thus-oxidized implants at a temperature between 120° C. and 750° C. for 5 to 120 minutes, and repeating once or twice the anodic oxidation and heat-treatment with the phosphate concentration, current density and temperature values as given above for the first step.

9 Claims, No Drawings

PROCESS FOR OBTAINING TISSUE-PROTECTIVE IMPLANTS PREPARED FROM TITANIUM OR A TITANIUM-BASE MICROALLOY

BACKGROUND OF THE INVENTION

This invention relates to a process for obtaining tissue-protective implants prepared from titanium or a titanium-base microalloy. More particularly, the present invention relates to a process for obtaining tissue-protective devices of bone surgery, especially cheek bone, mandible and common surgery, implants prepared from a medical-purity metal titanium and/or titanium-base microalloy, containing at least 98% of titanium, wherein a biocompatible (tissue-protective) coating is established by anodic oxidation on the metal surface after degreasing and chemical or electrochemical etching.

It is a known process to coat the metal implant with a hydroxyapatite (HA) layer by plasma-spray. This method of coating with HA types is described in detail by W. R. Lacefield ["Hydroxyapatite Coatings" in: Ann. N.Y. Acad. Sci. 523, 72–80 (1988)] as well as by K. A. Thomas et al. ["The Effect of Surface Macrotexture and Hydroxyapatite Coatings on the Mechanical Strength and Histological Profiles of Titanium Implant Materials" in: J. Biomed. Mater. Res. 21, 1395–1414 (1987)].

In case of layers applied by plasma-spray the bone formation becomes more rapid, the period of recovery becomes shorter and the connection of bone with the implant is more solid. These advantages are accompanied, however, by some difficulties: the composition of the HA layer applied depends on the technological procedure employed, the uniformity of the coating as well as of the size and shape are difficult to ensure, the absorption of the layer cannot be followed up and results of long-lasting experiments (10 to 20 year) are not available yet.

In general, the adhesion of the layers to the implants is not satisfactory and the free, polyvalent, e.g. $Ti^{4+}$ ions are toxic. In case of absorption into the bone of the HA layer a connection develops between the metal implant and the bone. These disadvantageous properties are discussed in detail in an article by L. Claes and K. Hanselmann: "Neue Biowerkstoffe, degradierbare Materialen und bioaktive Oberflächen," 2. Symp. Materialforschung 1991, pp. 155–180, 26–29th August 1991, Dresden.

According to the German patent specification No. 1,943,801 the tissue-protective behaviour of implant devices is improved by a coloured thin coating showing the interference colours of an oxide, nitride, carbide or carbon nitride. This process is based on the empirical recognition that the danger of inflammation following the implantation is reduced by using a coating. This patent does not contain, however, any detailed description of the process or essential information about the material quality.

There are known processes utilizing anodic oxidation of titanium for non-medical purposes such as that described in the German patent specification No. 2,216,432, according to which porous titanium oxide is prepared by using a sulfuric acid/hydrochloric acid electrolyte and a formation voltage lower than 46 V.

The colouring of titanium is carried out by using a sulfuric acid solution of 12 to 30% concentration and a formation voltage of 14 to 20 V according to the published Japanese patent application No. 56/58990. For the same purpose, a mixture of acetamide with one or more acid(s) is suggested by the published Japanese patent application No. 56/168894. According to the published Japanese patent application No. 62/161993 the oxidation of titanium is terminated by the heat-treatment of the anodic layer. According to the published Japanese patent application No. 63/18099 a coloured oxide layer is developed by the anodic oxidation of heat-treated titanium whereas according to the Japanese patent application No. 2/194,195 the oxide layer is formed by anodic oxidation carried out with a mixture of phosphoric acid and oxalic acid.

The known processes using anodic oxidation or their combination with heat-treatment result in coatings that are either porous or their thickness is lower than 1000 Å, so they are unsuitable to medical purposes.

SUMMARY OF THE INVENTION

The present invention is aimed to develop a corrosion-resistant, coherent oxide-ceramic layer of at least 2000 Å in thickness, which contains also a bioactive component, is built up from the material of the implant itself, has good adhesion properties and ensures an aesthetical appearance.

It is the object of the present invention to develop a process resulting in a biocompatible coating with coherent oxide-ceramic properties on implants prepared from titanium and/or titanium-base microalloys by combining electrochemical and thermochemical reactions.

The process according to the invention is based on the recognition that the anodic oxidation of implants in electrolytes is possible also in a voltage range over 100 V, which allows to prepare oxide layers with an amorphous structure and a thickness of 2000 to 2500 Å. These layers can be transformed to layers containing crystalline titanium dioxide of the anatase, brookite or rutile type by heat-treatment or vacuum heat-treatment. The extent of transformation into the individual phases can be controlled by the parameters of the heat-treatment. Thus, the layer is transformed as a whole to e.g. a transparent, colourless crystalline rutile layer at 700° C. in a vacuum oven within 60 minutes.

Furthermore, the invention is based on the recognition that an insulating titanium dioxide protective layer can be formed on the surface of the implant by suitable selection of the oxidation voltage in repeated anodic oxidations carried out through the crystalline oxide layer. Said protective layer has a characteristic colour ranging from violet through blue to golden yellow, does not show any change during the subsequent heat-treatment and retains its colour and ceramic properties.

Finally, the invention is based on the recognition that, in case of anodic oxidation carried out in the above manner, a few percentages of phosphate ($PO_4^{3-}$) and hydrogen phosphate ($HPO_4^{2-}$) anions are incorporated from the phosphate-containing electrolyte into the oxide layer formed on the implant surfaces and these anions further improve the biocompatible properties of the coating and promote bone integration.

Thus, the present invention relates to a process for obtaining tissue-protective devices of bone surgery, especially cheek bone, mandible and common surgery, implants prepared from a medical-purity metal, titanium and/or a titanium-base microalloy containing at least 98% by weight of titanium, by establishing a biocompatible (tissue-protective) coating on the metal surface by anodic oxidation after degreasing and chemical or electrochemical etching, which comprises carrying out the anodic oxidation of the etched implant surfaces in an aqueous solution of a phosphate concentration lower than 20% by weight with a current density of 2 to 50 mA/cm$^2$ until reaching a voltage of at least 105 V, then, after washing to ion-free, heat-treating the thus-oxidized implants at a temperature between 120° C. and 750° C. for 5 to 120 minutes, and repeating once or twice the anodic oxidation and heat-treatment with the phosphate concentration, current density and temperature values as given above for the first step.

DESCRIPTION OF THE PREFERRED EMBODIMENTS

According to the invention it is suitable to use a primary, secondary or tertiary orthophosphate and/or methyl ethyl phosphate as phosphate-containing bath and ammonium, potassium or sodium orthophosphate as primary orthophosphate.

When carrying out the heat-treatment under reduced pressure, it is suitable to increase the temperature to 680° to 740° C., preferably 710° to 720° C.

According to a preferred embodiment of the process of the invention the first anodic oxide layer is formed by using an aqueous solution containing 3 to 7% by weight, suitably 5% by weight of disodium hydrogen phosphate, and by oxidizing with a current density of 15 to 25 mA/cm$^2$, preferably 18 to 20 mA/cm$^2$, until reaching a voltage of 105 to 125 V, preferably 115 to 120 V.

The heat-treatment of the oxidized implants is preferably carried out in a temperature range of 300° to 450° C., suitably 350° to 380° C., for 5 to 120 minutes, preferably for 40 to 60 minutes. The pressure is maintained at atmospheric value in air or an inert gas, or under an overpressure of 100 to 200 Pa during the heating-up period.

In order to obtain a colourless, transparent oxide-ceramic coating, a vacuum heat-treatment is used at a temperature of 680° to 740° C., preferably 710° to 720° C.

In the second and third steps any of the electrolytes being useful in the first oxidation step or a mixture thereof can be employed to form the oxide layer. The value of the oxidation voltage is selected according to the colour desired of the implant coating: the colour of the coating is violet at 35 V, blue at 50 V and golden yellow at 115 V.

The process according to the invention is preferably used on implants, devices of cheek, mandible and common surgery devices, fixing elements, screws and tooth roots, conveniently prepared from a high-purity metal, titanium or a titanium-base microalloy containing at least 98% of titanium.

The main advantages of the process according to the invention can be summarized as follows.

a) The oxide-ceramic coating ensures the formation of a durable and solid connection between the implant and the bone due to the relatively fast growing of the bone into the solid oxide-ceramic coating (bone integration).

b) In addition to a high mechanical strength, the implant ensures excellent biocompatibility.

c) In biological media the oxide-ceramic layer is less toxic than the titanium metal itself.

d) The corrosion-resistance of titanium is extraordinarily (by several orders of magnitude) increased by the oxide-ceramic protective coating simultaneously inhibiting metal ions, mainly titanium(IV), iron(III), vanadium(V) and other ions releasing from the alloying elements, to enter the organism.

e) In case of a mechanical injury, the oxide-ceramic coating shows so-called "self-healing" properties due to spontaneous oxidation under effect of air and body fluids.

f) Aesthetic demands may also be satisfied by the coating since a number of colours (golden brown, violet, blue, greenish, golden yellow) can be produced without the use of any dye by varying the thickness of the coating and the voltage, resp.

g) The titanium-core implants covered with an oxide-ceramic coating retain their advantageous properties inclusive of colour stability even after repeated sterilization.

h) X-ray examinations as well as the preparation of computer-assisted and MR tomograms are rendered possible or not significantly influenced by the oxide-ceramic layer.

i) It is proven by clinical results that the so-called osteointegration process occurs in a more rapid and safer manner by using implants with an oxide-ceramic layer in comparison to implants without this coating.

j) In opposition to the implants possessing a protective layer applied by known processes, e.g. plasma-spray or isothermic compression as well as to implants provided with a calcium hydroxyapatite coating (of grade 5 according to the Mohs' hardness scale), a further advantage of the implants prepared by the process of the invention appears in a substantially higher hardness (of grade 6 to 6.5 according to the Mohs' hardness scale) of the oxide-ceramic coating, which makes possible to prepare e.g. HC-type surgical screws with an excellent hardness and self-holing edge as well as titanium roots with screw construction.

k) The adhesive strength between the oxide-ceramic coating and the titanium core is significantly higher in comparison to that produced by processes known in the art since the oxide-ceramic coating is actually not a layer formed by simple "application" but a protective layer grown on the surface of the titanium core itself, which possesses stabilized crystalline oxide-ceramic properties.

l) The oxide-ceramic coating ensures uniform and reproducible layer thickness, size and shape for the implant.

The process according to the invention is further illustrated by the following non limiting Examples.

EXAMPLE 1

Preparation of Tooth-Root Implants With a Golden Yellow Oxide-Ceramic Coating Tooth-root implants prepared from a titanium alloy used for implants, with a purity of about 99% with composition and properties Corresponding to the ISO 5832/II (Grade 4) standard, are etched at 45° C. for 3 minutes in an aqueous solution containing. 6% by weight of hydrogen fluoride (HF) and 23% by weight of nitric acid (HNO$_3$) and then washed until fluoride-free.

Subsequently, the tooth-root implants are anodically oxidized at 85° C. in an aqueous solution containing 5% by weight of disodium hydrogen phosphate (Na$_2$HPO$_4$) with a constant current density of 20 mA/cm$^2$ until reaching 114.5 V. Then the implants are further oxidized at a constant voltage for additional 60 minutes.

After washing, drying and heat-treatment carried out under atmospheric pressure at 350° C. for 30 minutes, the implants are repeatedly anodically oxidized at 85° C. in an aqueous solution containing 5% by weight of disodium hydrogen phosphate with a current density of 15 mA/cm$^2$ until reaching 112 V. Thereafter the oxidation is continued at a constant voltage of 112 V for additional 60 minutes. At this time the current density measured in the oxidizing bath and related to the oxidized pieces amounts to a few $\mu$A/cm$^2$.

After washing and drying the tooth-root implants are repeatedly heat-treated at 300° C. under an overpressure of 50 to 100 Pa for 30 minutes.

EXAMPLE 2

Preparation of Dental Surgery Screws With a Blue Oxide-Ceramic Coating

The first step of the oxide-ceramic coating process is carried out as described in Example 1 on so-called HC-type surgical screws used as safety ("emergency") screws (therefore prepared to blue colour for distinction) prepared from microalloyed titanium (containing about 98.8% of titanium) corresponding to the ISO 5832/II standard, with a self-holing edge [corresponding to the ISO 9268:1988 (E) standard], except that a solution containing 10% by weight of disodium hydrogen phosphate is used for anodic oxidation. However, in the second step following the first heat-treatment, the screws are anodically oxidized in an aqueous solution containing 1.5% by weight of ammonium dihydrogen phosphate (NH$_4$H$_2$PO$_4$) at 85° C. with a current density of 15 mA/cm$^2$ but only until reaching a voltage of 50 V. Thereafter the oxidation is continued at a constant voltage of 50 V for additional 60 minutes. Subsequently, a repeated heat-treatment is carried out at 300° C. under atmospheric pressure for 60 minutes.

The operations carried out in the second step are repeated in a third step, except that a current density of 3 mA/cm$^3$ is used, instead of 15 mA/cm$^2$.

EXAMPLE 3

Preparation of Connecting Surgical Fixing Sheets With a Violet-Coloured Oxide-Ceramic Coating The process of Example 1 is followed except that the heat-treatment in the first step is carried out at 150° C. for 110 minutes to obtain the oxide-ceramic coating or hole-containing sheet implants used for oral surgery and surgical fixing elements, prepared from a titanium alloy according to the ISO 5832/II standard.

However, in the second step following the first heat-treatment the connecting sheet implants are repeatedly oxidized at 85° C. in an aqueous solution containing 2% by weight of sodium orthophosphate (Na$_3$PO$_4$) with a current density of 20 mA/cm$^2$ until reaching a final voltage of 35 V. Then the oxidation is continued at a constant voltage of 35 V for additional 60 minutes. After washing and drying the sheet implants are heat-treated at 150° C. under atmospheric pressure for 110 minutes.

EXAMPLE 4

Preparation of Implants With a Colourless, Transparent Oxide-Ceramic Coating

The process described in any of Examples 1 to 3 is followed, except that both heat-treatments are carried out in a vacuum oven under reduced pressure at 720° C. for 10 minutes in the first step and for 30 minutes in the second step. During this period nearly the total amount of the oxide-ceramic layer being on the surface of the implant is transformed to a rutile-type transparent crystalline TiO$_2$ coating possessing a hardness of grade 6.5 according to the Mohs' hardness scale.

EXAMPLE 5

Preparation of Implants With a Golden Yellow Oxide-Ceramic Coating

The process described in Example 1 is followed, except that the first oxidation is carried out in an aqueous solution containing also 2.5% by weight of disodium hydrogen phosphate (Na$_2$HPO$_4$) in addition to 2.5% by weight of potassium dihydrogen phosphate (KH$_2$PO$_4$).

EXAMPLE 6

Preparation of Implants With a Violet Oxide-Ceramic Coating

The process described in Example 3 is followed except that in the second step the oxidation is carried out in an aqueous solution containing also 1% by weight of potassium orthophosphate (K$_3$PO$_4$) in addition to 1% by weight of sodium orthophosphate (Na$_3$PO$_4$).

EXAMPLE 7

Preparation of Implant With a Golden Yellow Oxide-Ceramic Coating

The process described in Example 1 is followed, except that the first oxidation is carried out in a solution containing 20% by weight of methyl ethyl phosphate to give a coating with excellent adhesiveness.

What is claimed is:

1. A process for obtaining tissue-protective devices of bone surgery, especially cheek bone, mandible and common surgery, implants prepared from a medical-purity metal, titanium and/or a titanium-base microalloy containing at least 98% by weight of titanium, by establishing a bio-compatible (tissue-protective) coating on the metal surface of the implant by anodic oxidation after degreasing and chemical or electrochemical etching, which comprises carrying out the anodic oxidation of the implant surface in an aqueous solution of a phosphate concentration lower than 20% by weight with a current density of 2 to 50 mA/cm$^2$ until reaching a voltage of at least 105 V, then, after washing to ion-free, heat-treating the implants at a temperature between 120° C. and 750° C. for 5 to 120 minutes, and repeating once or twice the anodic oxidation and heat-treatment with the phosphate concentration, current density and temperature values as given above for the first step.

2. A process as claimed in claim 1, which comprises using a primary, secondary or tertiary orthophosphate and/or methyl ethyl phosphate as phosphate-containing bath.

3. A process as claimed in claim 1, which comprises using an aqueous solution containing 3 to 7% by weight of disodium hydrogen phosphate as aqueous solution.

4. A process as claimed in claim 1, which comprises carrying out the heat-treatment of the implants for 5 to 120 minutes.

5. A process as claimed in claim 1, which comprises carrying out the anodic oxidation with a current density of 15 to 25 mA/cm$^2$ until reaching a voltage of 105 to 125 V.

6. A process as claimed in claim 1, which comprises carrying out the heat-treatment at a temperature of 300° to 450° C.

7. A process as claimed in claim 1, which comprises carrying out the heat-treatment at a temperature of 680° to 740° C. under vacuum.

8. A process as claimed in claim 2, which comprises using ammonium, potassium or sodium orthophosphate as primary orthophosphate.

9. A process as claimed in claim 5, which comprises carrying out the heat-treatment for 40 to 60 minutes.

* * * * *